United States Patent
Herbst et al.

(10) Patent No.: US 6,708,066 B2
(45) Date of Patent: Mar. 16, 2004

(54) ELECTROCHEMICAL TREATMENT OF TISSUES, ESPECIALLY TUMORS

(76) Inventors: Ewa Herbst, c/o Ewa Herbst & Assoc., P.O. Box 89, Edgewater, NJ (US) 07020; Benedict Aurian-Blajeni, c/o Ewa Herbst & Assoc., P.O. Box 89, Edgewater, NJ (US) 07020

( * ) Notice: Subject to any disclaimer, the term of this patent is extended or adjusted under 35 U.S.C. 154(b) by 111 days.

(21) Appl. No.: 09/733,023

(22) Filed: Dec. 8, 2000

(65) Prior Publication Data
US 2001/0021868 A1 Sep. 13, 2001

(51) Int. Cl.⁷ .................................................. A61N 1/05

(52) U.S. Cl. ............................ 607/115; 607/21; 607/3; 607/98; 514/16

(58) Field of Search ......................... 607/2, 3, 20–23, 607/98–102, 115–120; 604/890.1, 19–23, 500, 501; 606/25–31, 45–50; 514/16

(56) References Cited

U.S. PATENT DOCUMENTS

| | | | | |
|---|---|---|---|---|
| 5,458,597 A | * | 10/1995 | Edwards et al. | 604/41 |
| 6,139,538 A | * | 10/2000 | Houghton et al. | 604/515 |
| 6,233,482 B1 | * | 5/2001 | Hofmann et al. | 604/21 |
| 6,319,901 B1 | * | 11/2001 | Bernard et al. | 514/16 |

* cited by examiner

Primary Examiner—Mark Paschall

(57) ABSTRACT

A technique and apparatus therefor adapted to treat in situ specified tissue, especially a malignant tumor, use being made of electrodes implanted in the tissue at spaced positions. Applied across the electrodes is a voltage causing a current to flow through the tissue to be treated. This current in one embodiment of the invention produces an electrochemical reaction yielding multiple reaction products, some of which are cytotoxic agents destructive of cancer cells, the voltage being regulated to optimize the yield of those agents having the greatest efficacy. In another embodiment, fed to the tissue is one or more reagents which when current flows through the tissue react with the material of an electrode to yield a cytotoxic agent in situ. Alternatively, the surface of the electrode can serve as a catalyst for the formation of the cytotoxic agents.

45 Claims, 1 Drawing Sheet

ELECTROCHEMICAL TREATMENT OF TISSUES, ESPECIALLY TUMORS

RELATED APPLICATIONS

This application is related to PCT application serial number US99/29564, filed Dec. 10, 1999, and designating the United States of America among other countries; the entire disclosure of that application is incorporated herein by reference.

BACKGROUND OF THE INVENTION

1. Field of Invention

This invention relates generally to the electrochemical treatment of tissues by applying a voltage across electrodes to cause a current to flow through the tissue. In one embodiment of the invention, the current flow produces an electrochemical reaction yielding multiple reaction products some of which act as cytotoxic agents to destroy cancer cells, the voltage being regulated to optimize the yield of those cytotoxic agents having the greatest efficacy. In another embodiment, fed into the tumor is one or more reagents which when current flows through the tumor react with the material of an electrode to yield a cytotoxic agent. Alternatively, the surface of the electrode can serve as a catalyst for the formation of the cytotoxic agents.

2. Status of Prior Art

Oncology is the branch of medical science dealing with tumors. The prime concern of the present invention is with treatment of tumors and other forms of neoplasm. The distinction between a benign and a malignant tumor is that the latter will invade surrounding tissues and spread or metastasize to other sites, whereas a benign tumor will not spread.

The common practice in the field of oncology to cure or ameliorate a cancerous condition is by appropriate surgery, radiotherapy or chemotherapy, sometimes used singly, but more often in combination.

Radiotherapy which produces its biologic effect on cancerous tissue by ionization is carried out by megavolt energy radiation in the form of X-rays from a linear accelerator or gamma rays from a cobalt 60 source. Radiation is highly penetrating, but in order to reach the region of the tumor being treated, the radiation beam must pass through regions containing healthy tissue and may therefore destroy these as well as the malignant tumor.

Chemotherapy dictates the utmost care in monitoring and controlling the administration of cytotoxic drugs, for the biochemistries of malignant and non-malignant cells are so similar that it is difficult to destroy cancerous cells without concurrently destroying healthy cells. The adverse effects of chemotherapy are notorious.

One of the most potent an widely used substances in the chemotherapy today is cisplatin (Cisplatin: Chemistry and Biochemistry of a Leading Anticancer Drug, Bernhard Lippert, Ed, Wiley, VCH, Weinheim, 1999). It is a platinum compound, first observed to form by electrochemical reaction in a cell culture by Barnett Rosenberg et al (Inhibition of Cell Division in *Escherichia coli* by Electrolysis Products from Platinum Electrode, Nature, Vol. 205, pp. 698–9, 1965). This work resulted in discovery of cisplatin as cytotoxic agent, highly effective in cancer treatment. Follow-up work by Rosenberg and co-workers showed that several platinum compounds have antitumor properties (Platinum Compounds: a New Class of Potent Antitumor Agents, Nature, vol. 222, pp. 385–6, 1969). Some other platinum group compounds have also been shown to destroy cancer tissue.

Both cisplatin and other platinum compounds are manufactured synthetically and administered, in most cases, intravenously. The major problem with chemotherapy drugs is a lack of selectivity (both cancerous and normal tissues are affected) and high toxicity for healthy tissue. In the case of cisplatin, there are severe side effects in form of kidney toxicity and nausea and vomiting. The kidney toxicity is currently controlled by hydration and the nausea and vomiting by drugs. Thus the intravenously administered doses currently used are limited by patient's tolerance to the drug rather than being optimized for dose effectiveness in cancer treatment.

In the case of solid tumors, experimental efforts are being made to minimize the side effects through a local delivery either through an injection of the anticancer agent directly to the tumor or through release of various anticancer agents encapsulated in e.g., hydrogels.

It is also known to destroy malignant tumors by elevating the temperature of the tumor to a level at which cancerous cells are destroyed. One method used for this purpose is to focus a beam of microwave energy of the type generated in a microwave oven onto the tumor. But the drawback of this technique is that healthy tissues through which the beam must pass to reach the tumor have a higher moisture content than the interior of the tumor and are therefore more reactive to microwave energy.

The problem with surgery to excise a malignant tumor is that the location of the tumor, as in the case of a tumor in the brain, may be such as to render the tumor inoperable. But even where the tumor is accessible to the surgeon's scalpel, then in order to reach this tumor, one must cut through and damage healthy tissue. Moreover with surgery, one cannot be sure that all malignant cells have been removed, and the residual cells may metastasize.

The primary concern of the present invention is with in situ electrochemical treatment of a malignant tumor, the treatment acting to destroy the tumor with minimal damage to regions surrounding the tumor.

In an existing electrochemical treatment (ECT), electrodes are implanted at spaced positions in or around the malignant tumor to be treated. Applied across these electrodes is a low dc voltage usually having a magnitude of less than 10 volts, causing a current to flow between the electrodes through the tumor. Due to an electrochemical reaction, reaction products are yielded which include cytotoxic agents that act to destroy the tumor.

In the ECT technique disclosed by Li et al., in Bioelectromagnetics 18:2–7 (1997), in an article "Effects of Direct Current on Dog Liver: Possible Mechanisms For Tumor Electrochemical Treatment" two platinum anode and cathode electrodes were inserted in a dog's liver with a 3 cm separation therebetween. Applied across these electrodes was a dc voltage of 8.5 volts, giving rise to an average current through the liver of 30 mA. This was continued for 69 minutes, with a total charge of 124 coulombs. The concentration of selected ions near the anode and cathode were measured. The concentration of $Na^+$ and $K^+$ ions were found to be higher around the cathode, whereas the concentration of $Cl^-$ ions was higher around the anode. Water content and pH were determined near the anode and cathode, the pH values being 2.1 near the anode and 12.9 near the cathode. The released gases were identified as chlorine at the anode and hydrogen at the cathode. The series of electrochemical reactions which took place during ECT resulted in the rapid and complete destruction of both normal and tumor cells in the liver.

Another example of ECT appears in the article "Electrochemical Treatment of Lung Cancer" by Xin et al. in Bioelectromagnetics 18:8–13 (1997). In this ECT procedure platinum electrodes were inserted transcutaneously into the tumor, the voltage applied thereto being in the 6–8 volt range, the current being in the 40 to 100 mA range, and the electric charge, 100 coulombs per cm of tumor diameter.

According to this article, the clinical results indicate that ECT provides a simple, safe and effective way of treating lung cancers that are surgically inoperable and are not responsive to chemotherapy or radiotherapy.

Also disclosing an ECT technique is the patent to Anderson U.S. Pat. No. 5,360,440 In Situ Apparatus For Generating An Electrical Current in a Biological Environment."

Electrochemical reactions as a function of pH and electrode potential can be predicted by means of a Pourbaix diagram, as disclosed in the Atlas of Electrochemical Equilibria in Aqueous Solutions—Pergamon Press, 1966—by Pourbaix. Reaction products of electrolysis of water include hydrogen, oxygen, and hydrogen peroxide ($H_2O_2$).

In the text Methods in Cell Biology, Vol. 46—Cell Death—published by Academic Press, 1995, it is noted (page 163), that hydrogen peroxide has been reported to be an inducer of cell death in various cell systems. This type of cell death is attributed to the direct cytotoxicity of $H_2O_2$ and other oxidant species generated from $H_2O_2$.

The present invention also involves an electrochemical technique for cancer treatment in which cisplatin, a highly-effective cytotoxic agent, or other cytotoxic agents are produced in situ. Of background interest therefore is the article in the Jul. 5, 1999 issue of The Scientist "From Basic Research to Cancer Drug, The Story of Cisplatin."

SUMMARY OF THE INVENTION

In view of the foregoing, the main object of this invention is to provide an electrochemical technique and apparatus for carrying out this technique adapted to treat, in situ, a tissue to destroy all or a selected portion thereof for the benefit of the patient, and most especially for treating a malignant tumor or other form of neoplasm in order to destroy cancerous tissues with minimal damage to healthy tissues.

A significant feature of one embodiment of this invention in which a voltage is applied across working and counter electrodes implanted in or otherwise applied to the tissue being treated, is that the voltage is controlled during electrochemical reactions produced in the tissue to optimize the yield of those reaction products which act as cytotoxic agents destructive of cells of that tissue type.

Also an object of this invention is to provide method and apparatus for carrying out an ECT procedure concurrently with chemotherapy treatment to subject the tissue being treated to one or more cytotoxic chemicals from a chemotherapy source as well as from reaction products yielded by an electrochemical reaction.

Yet another object of this invention is to provide a method and apparatus for carrying out an ECT procedure in conjunction with photochemically-activated drugs delivered to the tissue, especially a malignant tumor, whereby as current passes through the tumor to produce an electrochemical reaction, the tumor is at the same time exposed to light to activate the drugs.

Briefly stated, these objects are attained by a technique and apparatus therefor adapted to treat in situ a specific tissue, especially a malignant tumor, use being made of strategically placed electrodes. In one embodiment of the invention, there is applied across the electrodes a voltage causing a current to flow through the tissue producing an electrochemical reaction yielding multiple reaction products, at least one of which is a cytotoxic agents destructive of the particular tissue cells desired to be eliminated. Coupled to the electrodes is a control unit which acts to regulate the voltage applied thereto so as to optimize the yield of those cytotoxic agents having the greatest efficacy. Strategic placement of the electrodes means that they are placed in situ effective to cause current flow through the tissue, and preferably to minimize current flow through other tissues not desired to be treated.

In another embodiment, one or more reagents are delivered to the tissue treated when current flows therethrough and react with the material of an electrode to yield a cytotoxic agent in situ, or an inactive isomer of a cytotoxic agent, which when exposed to light becomes activated.

In yet another embodiment one or more reagents are delivered to the tissue and the surface of the electrode serves as a catalyst for the formation of the cytotoxic agents in situ.

In still another embodiment, the electrode composition itself (such as the anode whose composition goes into solution during the electrochemical treatment) is a cytotoxic agent, or reacts with a second composition delivered locally to form a cytotoxic composition in situ.

BRIEF DESCRIPTION OF THE DRAWINGS

For a better understanding of the invention, as well as other objects and further features thereof, reference is made to the following detailed description to be read in conjunction with the accompanying drawings, wherein.

DETAILED DESCRIPTION OF SPECIFIC EMBODIMENTS

Tissue can be defined as "an aggregation of similar cells and their intercellular substance" (Blackiston's Pocket Medical Dictionary, McGraw-Hill, 1960). For example, this definition includes such tissues as: soft, hard, healthy, diseased, muscle, neural, bone, tendon, cartilage, dental, periodontal, fat, blood vessels, brain, skin, fascia, tumor (either benign or malignant), other forms of neoplasm, and other tissues existing in biological organisms. This invention is applicable to those and all other tissues, as well as to plant tissues. Accordingly, in the broadest sense as used herein, a "patient" includes human and non-human mammals and other animals, as well as plants (i.e., multicellular organisms). For ease of discussion, the invention will be described with respect to tumors, be they malignant or benign.

In general, the invention relates to the use of electrodes to effect a cytotoxic effect on selected tissue. The placement of the electrodes is strategically done such that current passing between the electrodes also passes through the tissue to be treated. There are at least two electrodes (anode and cathode), and there may be more than one anodic and/or cathodic electrode. Thus, the strategic placement of the electrodes means that in three-dimensional space, a line between an anode and a cathode passes through the tissue to be treated. For example, all of the electrodes may be placed outside of the tissue to be treated, one or more may be placed inside (or otherwise in contact with) the tissue to be treated, or all of the electrodes may be placed inside the tissue to be treated.

The cytotoxic effect can be accomplished by the creation, in situ, of a cytotoxic agent. Generation of a cytotoxic agent locally can be accomplished in a number of ways which are not mutually exclusive of each other. As discussed below, a precursor compound can be introduced in the area of (or into) the tissue to be treated wherein current between the electrodes modifies or changes the precursor compound into a cytotoxically active compound. Another way of producing such a compound is to introduce locally to the tissue to be treated a compound that reacts with, and thus may consume, an electrode, the reaction product being cytotoxic; or the reaction product(s) may be further modified by the current passing between the electrodes and transformed into a cytotoxic agent; or the reaction product may react with a second compound introduced locally to form a cytotoxic agent.

First Embodiment

Figure 1:
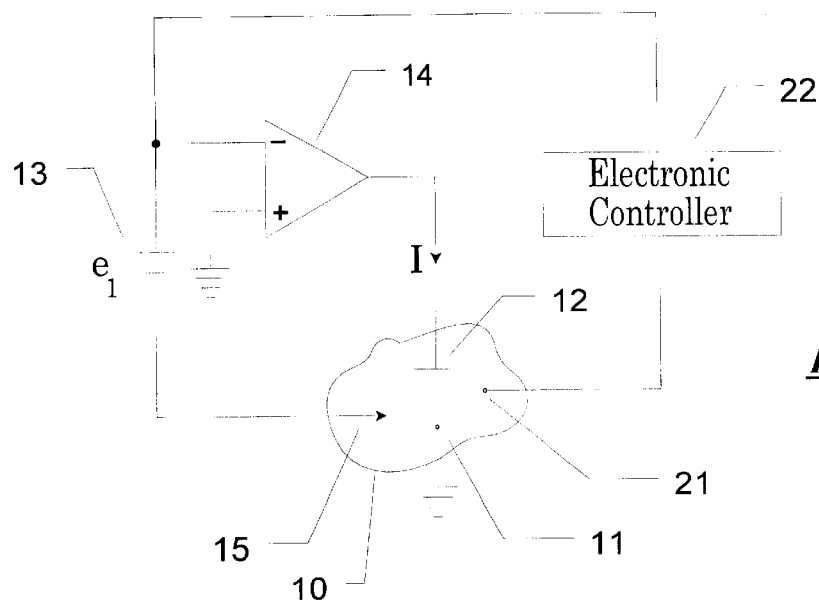
FIG. 1 is a schematic diagram of an electrochemical treatment system (ECT) in accordance with the invention for destroying a malignant tumor or other form of neoplasm. It depicts two alternative feedback systems.

Shown in FIG. 1 is an ECT system in accordance with the invention for treating a malignant tumor 10. The treatment is carried out in situ by passing a current through the tumor to produce an electrochemical reaction therein yielding reaction products some of which have cytotoxic properties. The electrochemistry of the tumor depends on its biological nature. Thus the bodily solutions permeating a cancerous liver are different from those found in a cancerous pancreas and the electrochemical parameters should be adjusted accordingly.

Typical reaction products resulting from passing current through tissues are hydrogen and oxygen, as well as chlorine and hydrogen peroxide. Hydrogen peroxide, which is a highly probable intermediate, is known to have strong cytotoxic properties, whereas other reaction products yielded in an ECT procedure vary in their effectiveness in destroying cancer cells. In an ECT system in accordance with the invention, the system operates to optimize the yield of those reaction products that have the greatest ability to destroy cancer cells.

In the system shown in FIG. 1 there are implanted in tumor 10 a working electrode 11 and spaced therefrom, a counterelectrode 12. These electrodes may be formed of platinum or other noble metals or alloys thereof. Or the electrodes may be formed of other metals or alloys thereof, such as titanium, tantalum, tungsten and stainless steel. Electrodes made of conductive oxides, nitrides (for example TiN), and semiconductors can also be used. Also various forms of carbon, such as activated carbon and glassy carbon can be used in electrode materials. The surface of the electrode may be further processed, for example by ion implantation or chemical vapor deposition, or coated with other materials.

In practice, the electrodes, especially the counterelectrodes, are preferably fabricated of porous material to enlarge their effective surface area and thereby reduce the current density, i.e., current per unit crossectional area of the electrode. Also more than one counterelectrode can be used in conjunction with one working electrode in order to distribute the current flow throughout the tumor.

Applied across electrodes 11 and 12 to cause a current to flow through the regions of the tumor bridging these electrodes is a voltage derived from a voltage source 13 under the control of a potentiostat or other feedback system 14, that maintains the electrode potential or the preset level of the quantity measured by the sensor.

A potentiostat is an instrument used in an electrochemical process which is adapted to automatically control the potential of a test or working electrode, with respect to a reference electrode, to within certain limits during an electrochemical reaction. Potentiostat 14 in the system disclosed in FIG. 1 acts to govern the voltage derived from voltage source 13 which is applied to working electrode 11 so that the multiple reaction products yielded by the electrochemical reaction when current passes through tumor 10, include products which have the cytotoxic properties most effective in destroying cancer cells.

Potentiostat 14 maintains at a substantially constant level the potential difference between working electrode 11 and the electrochemical solution in tumor 10 (the working electrode potential) measured with respect to a reference electrode 15. Reference electrode 15 is implanted in the tumor as close as possible to the working electrode 11.

Current through tumor 10 is controlled by potentiostat 14 so that the reference electrode 15 is at $-e_1$ vs. ground. Since working electrode 11 is grounded, $e_{working}$ (vs. reference) is equal to $e_1$ regardless of fluctuations in the impedance of tumor 10. The arrangement shown in FIG. 1 is a simplified version of the potentiostat arrangement. In practice, a more complex arrangement may be provided to obviate drawbacks. In the simplified design none of the input terminals are at true ground.

The potential to be maintained on working electrode 11 by potentiostat 14 is that potential which, for the tumor being treated, gives rise to a current flow through the tumor that produces an electrochemical reaction therein yielding those reaction products which include cytotoxic agents having the greatest ability to destroy cancer cells.

For example, if it is determined empirically that the volume of hydrogen peroxide, a highly effective cytotoxic agent, included in the multiple reaction products yielded by the electrochemical reaction reaches its highest level when the potential of the working electrode is in the 1.00 to 1.25 volt range, then the potentiostat system is adjusted to maintain the potential in this range. Or the potentiostat system may operate in whatever other range that yields reaction products having optimal cytotoxic characteristics.

In order to operate the system so that it automatically maintains the voltage in the desired range with respect to a selected variable in the electrochemical process indicative of the desired cytotoxic reaction products being generated, this variable is sensed by a sensor 21. The variable being sensed may be pH or $pO_2$ in the vicinity of the counterelectrode or at the working electrode instead of the electrode potential, where pH is the measure of the concentration of hydrogen ions, while $pO_2$ is a measure of partial pressure of oxygen.

Sensor 21 produces an electrical signal that depends on the variable being sensed, for example pH, this signal being applied to an electronic controller 22 which compares the signal with a set point signal to produce an error signal that depends on the deviation of the sensor signal from the set point; that is the extent to which the sensed pH deviates from the pH value that corresponds to an optimum condition.

Controller 22 is coupled to potentiostat 14 acting to adjust the system to maintain the desired potential of the working electrode at which the ECT system is most effective in destroying cancer cells.

To minimize polarization at the electrodes of the electrochemical system, the polarity of the voltage applied to the electrodes may on occasion be reversed. And the voltage applied to the electrodes need not be continuous, but may be pulsed or varying in a regular manner, like a sine wave or a triangular wave or any other periodic wave, or randomly varying, or varying in a preset manner.

The nature and the shape of the electrodes should be appropriate to the tumor or other form of neoplasm being treated. For example the strength, pliability, flexibility, material, textural parameters like roughness and surface area, and the shapes and geometry of the electrodes are important for achieving desired results. Electrodes of various shapes, such as flat, spherical or shaped as screws or cannulae, or made of fibers, can be manufactured with low or high surface porosity to affect their surface area. Highly porous electrodes will have large surface area and exhibit lower polarization potential.

Thus in the case of skin cancer, the electrodes can then be applied to the skin surface, and for this purpose flexible patch electrodes are suitable. Flexible patch electrodes can also be used subcutaneously placed over a larger surface area under treatment. In the case of tumors in which the electrodes are to be implanted, the appropriate electrodes depend on the character of the tumor. Thus with a soft tumor, the electrode may take the form of a flexible pin or helical wire capable of penetrating the tumor, whereas for relatively hard tumors, a screw-type electrode may be preferable. In the case of bone tumors, a bone electrode or multiple bone electrodes, such as, e.g., those described in patents U.S. Pat. Nos. 4,683,896 and D298,168 to Ewa Herbst and Lars Botvidsson and incorporate herein by reference, can be utilized. In the case where the electrodes are wholly or partially insulated, one or more areas of treatment delivery can be created by leaving appropriate openings in the insulation material.

Figure 2:
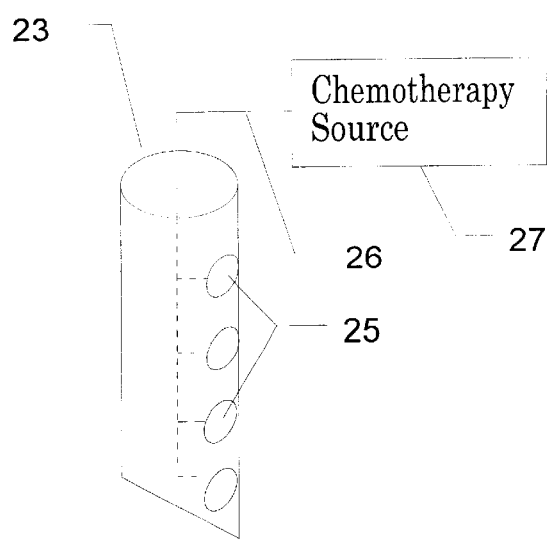
FIG. 2 illustrates an electrode included in an ECT system adapted to deliver a chemotherapy drug or other substance, utilized in synthesis in situ, to the tumor being treated.

In some instances it may be desirable to combine chemotherapy with an ECT procedure either concurrently or alternately. For this purpose, as shown in FIG. 2, either the working electrode or the counterelectrode may take the form of a hollow tubular rigid electrode 23 having a cutting tip 24 to facilitate its insertion in a tumor. Or a flexible catheter-like electrode can be used with an optional insertion guide. Both can be insulated, partially insulated or exposed.

Electrode 23 may be provided with one or more of apertures 25 along its length, or it may be shaped as a cannula and optionally having one or more apertures along its length. Delivered through a suitable line 26 feeding electrode 23 is a flowable substance from a source 27. Hence in this arrangement, the tumor can be subjected to a cytotoxic agent derived from a chemotherapy source as well as cytotoxic agents yielded by the electrochemical ECT process or other substance utilized in the synthesis in situ.

In treating a malignant tumor it is vital that no portion thereof remains untreated, for untreated residual tissue may spread with serious consequences. By combining chemotherapy with an ECT procedure, one is then able to ensure fuller treatment of the tumor.

Another approach to combining chemotherapy with an ECT procedure is to use a photochemically activated drug which is absorbed by the tumor, or delivered thereto through the electrodes, but until such time as it is activated by light energy, remains inactive and innocuous.

Figure 3:
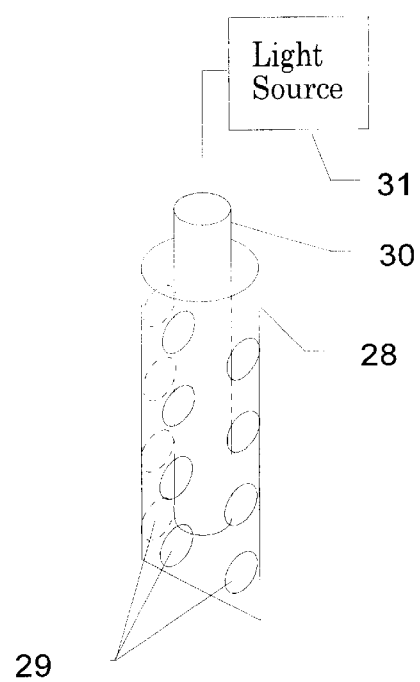
FIG. 3 illustrates an electrode to be included in an ECT system adapted to apply light energy to a tumor being treated.

For this purpose, the electrode 28, as shown in FIG. 3 is hollow and has one or more apertures 29 which are circumferentially distributed. Received within the hollow electrode is a flexible fiber optics light pipe 30 which is coupled to an external high-intensity light source 31.

Thus when the tumor impregnated with the light-activatable drug undergoes an ECT procedure, the tumor is at the same time (or in alternate sessions) subjected to light energy to activate the drug, thereby releasing cytotoxic agents whose activity is combined with the agents released as reaction products. While we have disclosed means to regulate the voltage applied to the electrodes, in lieu thereof, use may be made of means to regulate the current flowing through the tumor to optimize the yield of cytotoxic agents having the greatest efficacy.

The treatment may be customized for each type of condition. In some cases, such as skin cancer, the treatment will be at the skin surface. In other cases, such as breast cancer or when the activation of the immune system is sought, the necessity of transcutaneous or implanted electrodes may arise.

The manner in which the treatment is administered depends on the type of cancer, being treated. For example, in solid tumors, the electrodes will be either implanted in the tumor, or in its immediate vicinity. The position of the electrodes could be one of the following, with the reference electrode preferably in close proximity to the working electrode, either inside or outside of the tumor:

a) the working electrode in the interior of the tumor and the counter electrode in the interior of the tumor;

b) the working electrode in the interior of the tumor and the counter electrode outside the tumor;

c) the working electrode outside the tumor and the counterelectrode in the interior of the tumor;

d) both electrodes outside the tumor.

One or both active electrodes (working and counter) can be replaced by several separate electrodes. For example, the working electrode can be placed at the center of the tumor, while two or more counter electrodes are placed around the tumor. The distance between the electrodes will be from about 0.5 mm to the maximum allowed by the extent of the tumor, in the case of localized tumors, or at the latitude of the physician.

As a treatment option, the material and the electrical potential of the electrodes are chosen in such a way that the appropriate agents (e.g. free radicals, protons, ions, etc.) are generated to influence the environment around the electrodes. The electrode material and potential are chosen to release or activate components of cancer killing agents and agents active in stimulating the immune system. These agents can be a part of the electrode material itself or can be administered locally or systemically.

The electrical charge can be applied in several regimens including various combinations of continuous and intermittent application of the electric component of the treatment at constant values of electrode potential or at variable values, where the shape (waveform) of the variation can be periodic or irregular. Examples are cyclic or pulsed administrations of the treatment. When the treatment is applied in conjunction with another form of therapy, such as chemotherapy or radiation therapy, the administration can be concomitant or alternative, in any sequence of administration sessions. For example, one or more sessions of one treatment can be administered before another treatment.

The light delivery through the fiber optics can also be carried out in various regimens. Thus, for example, light can be delivered continuously or intermittently, at a single or multiple wavelengths, etc. The light delivery can occur concomitantly, alternatively, or in overlapping time intervals with the electrical charge delivery.

Second Embodiment

As pointed out previously, though cisplatin is a highly potent anti-tumor agent and is widely used in chemotherapy, it usually has severe systemic side effects.

In an electrosynthesis method in accordance with the invention, the cisplatin, or other Pt compounds, are produced in situ and therefore are confined to the tumor and its vicinity. In this method, electrodes are implanted in the tumor or placed in its immediate vicinity and current is caused to flow therethrough between the electrodes in the course of which a cytotoxic agent is synthesized in situ by a reaction between the material of the electrode and a substance delivered to the tumor. Hence the synthesis process is electro-assisted.

Among the advantages of this method are the following:

I. In situ synthesis makes it possible to create and utilize labile cytotoxic agents which are potent yet degrade rapidly and have a short effective life. Hence the agent works quickly on the interior of the cancerous tumor, yet shortly thereafter ceases to be effective so that minimal damage is inflicted on healthy tissue external to the tumor and the whole organism.

II. By adjusting, controlling or regulating the current flowing between the electrodes through the tumor or by varying its intensity, shape or polarity, it becomes possible to deliver in situ to the tumor a desired and precise dosage of the synthesized cytotoxic agent.

A preferred mechanism for producing cisplatin in situ in a cancerous tumor is to implant electrodes therein at least one of which is formed of platinum. Injected into the tumor or otherwise delivered in thereof is an ammonium chloride solution. When current passes through the tumor between the electrodes, the substance then reacts with the platinum electrode to produce cisplatin in a dosage that is optimized by controlling the current flow. Other Pt compounds or different cytotoxic agents can be synthesized in situ in a similar way. One example is gallium nitrate $Ga(NO_3)_3$. Although gallium is a liquid at the body temperature, it can be part of electrode by alloying. Gallium has no known adverse biological effects and is currently considered as one of the components of dental restoration alloys (Galloy), with In and Sn. Alloys of gallium with copper are commercially available (ACI), as are alloys with Pt (95% Pt, 2.5% Ga and 2.5% Au or In) used in jewelry. It will dissolve electrochemically with ease, having a standard reduction potential of −0.560 V vs NHE (cf. Cu 0.521 V and Zn −0.7618). Gallium nitrate can thus be prepared by the electrodissolution of the electrode.

In practice those or other reactions may take place between the electrode and the reagent introduced into the tumor, with a hollow electrode or a catheter used for delivery. Or between two or more substances either naturally occurring in the organism or introduced into the tumor, with the electrode having an electrocatalytic effect. In other words, the material of the electrode controls the course and/or the speed of reactions whose products are cytotoxic.

One way of carrying out a method is by potential-controlled reaction at the electrodes implanted in the tumor. Another way in accordance with the invention is by using hollow electrodes or a catheter for adding an appropriate substance to ensure the proper chemical environment for the formation of the cytotoxic agent in situ. Still another way is by continuously or intermittently releasing in situ from an implanted reservoir (one embodiment is a hydrogel capsule) appropriate substances to ensure the proper chemical environment for the formation of the cytotoxic agent in situ. Such time-released substances, activated electrically when needed, can be applied over extended periods of time including a period after the main treatment has been completed, to prevent a reoccurrence of cancer. In the case of creation of cisplatin, an ammonium-containing substance needs to be present in the environment, as well as chloride ions. These can also be used to activate the immune system response.

The same method can be used to produce in situ non-cytotoxic agents, which can later be converted to the cytotoxic agents by isomenzation. Isomerization is a process whereby a compound is changed into one of its isomers; i.e., one of two or more chemical substances having the same elementary percentage composition and molecular weight but differing in structure, and therefore in properties. An example thereof is transplatin and cisplatin. While cisplatin is highly cytotoxic, transplatin is considered not to be.

Isomerization of transplatin to cisplatin can take place in the presence of light. Photo assisted isomefzation in situ can be performed by introducing a non-cytotoxic isomer into the tumor and exposing it to the light. In the present invention, electrosynthesis in situ of a non-cytotoxic isomer can be combined with a photo-assisted isomenzation to transform a non-cytotoxic isomer to a cytotoxic one by exposing it to the light. This can be done by means of optical fibers introduced to a tumor via a hollow electrode or catheter.

In an electrosynthesis method in accordance with the invention for producing a cytotoxic agent, in situ, the preferred electrode material is from the platinum group, namely Ruthenium (Ru), Rhodium (Rh), Palladium (Pd), Osmium (Os), Irridium (Ir) and Platinum (Pt). The substance usable with each of these metals is a reagent that reacts with the metal to produce a cytotoxic agent.

The invention is not limited to metals in the platinum group. As pointed out in the article by Kopf-Maier, "Complexes of metals other than platinum as antitumor agents", Eur. J. Clin. Pharmacol. 1994; 47(1):1–16, numerous non-platinum metals are effective against tumors. These comprise main group metallic compounds of gallium, germanium, tin and bismuth, early transition metal complexes of titanium, vanadium, niobium, molybdenum, rhenium and late transition metal complexes of copper and gold in addition to platinum group metals. Thus in addition to platinum complexes several non-platinum antitumor agents have entered clinical trials. Gallium trinitrate and spiro-germanium have shown limited cytostatic activity against some human carcinomas and lymphomas in Phase II clinical studies. Unusual patterns of organ toxicity in man was found with early transition metal complexes butotitane and titanocene dichloride.

In practice, means may be included operating in conjunction with the electrodes implanted in the tumor to sense the presence of the cytotoxic agent produced in the course of the electrosynthesis process and to produce a signal whose magnitude is indicative of the potency of this agent. This signal is then used to control the current flowing through the tumor so as to optimize the potency of the agent.

One suitable device for providing and controlling the electrical signals is disclosed in a U.S. Pat. No. 6,029,090 "Multi-Functional Electrical Stimulation System" to Ewa Herbst, the disclosure of which is incorporated herein by reference.

Dose-Response Experiment

In a proof of principle experiment, Controlled Potential Electrochemical Treatment (CPECT) was applied to a T47D breast cancer cell line. The cells were plated in 100 mm diameter Petri dishes in RPMI 1640 culture medium. Platinum electrodes were used for treatment. Two concentric electrodes were made of platinum wire with the larger one being counter electrode to minimize the effects of polarization. For reference, a platinum quasi-reference electrode was used since it is usually within 20 mV from the hydrogen reversible potential. In the first attempt to determine if there is a correlation between cell death and various electrode potentials, we simultaneously treated six culture dishes: one with 1.3V; two with 1.2V; one with 1.05V; one with 0.9V; and one with 0V with respect to a reference electrode. Two additional culture dishes served as controls without any electrodes present. Due to a bad electrode connection, the 1.3V experiment had to be excluded from evaluation.

The treatment was applied for 30 minutes, after which time all dishes were evaluated visually with respect to any bubbles visible around the electrodes, as well as any microscopic changes to the cells such as detached, floating cells. Normally T47D cells are attached to the bottom of the culture dish; floating cells are dead cells. After the visual evaluation, culture dishes were placed in the incubator for 24 hours and evaluated the next day for cell survival using staining with trypan blue, a dye which is taken up by dead cells only. The number of both viable and dead cells was calculated using a hemocytometer.

Results of this preliminary experiment showed a massive cell death in one dish with 1.2V electrode potential and a clear case of electrolysis, as evidenced by whole 40 mm diameter center (encircled by a working electrode) as well as an area above the counter electrode full of bubbles. Some bubbles were also visible in the other 1.2V and in the 1.05V dish, although with only minimal cell death. The experimental methods used in this rough experiment were not sophisticated enough to evaluate correctly differences in the cell death between those potentials. Results of the 0.9V and at 0V dishes evidenced no bubbles that were visible. The current in the dishes below 1.2V potential was in the range 0.3 mA–1.0 mA. The current in the dish with 1.2V potential, where a massive cell death took place, increased over 30 min. from 11 mA to 49 mA. The pH in the culture media was in the range of 7.2–7.4 and remained constant in the bulk of the solutions, although there probably were changes in the vicinity of the electrodes.

Several methods are available to more accurately define the dose response in the future, i.e. the relationship between the level of the electrical stimuli and the resulting cell death. Those methods can also distinguish between the two types of cell death: necrosis and apoptosis. Necrosis is typically a result of some external insult which leads to a breakage of the cell membrane, which often leads to an undesirable inflammatory reaction in vivo. Apoptosis, or self death, is due to breakage of the DNA strands inside the cell without a disrupting of the membrane. Apoptosis is a normal cell control process in the body. By imitating nature, a set of appropriate environmental conditions can be created using correct electrical stimuli and the apoptotic reaction can be initiated. A potential reaction path for apoptosis is: hydrogen peroxide, $H_2O_2$, which can be a product of electrochemical reaction, passes through a cell membrane and reacts with transition metal ions, such as iron, $Fe^{2+}$ or possibly copper $Cu^+$; inside the cell creating hydroxyl radical OH., which in turn acts upon DNA causing single strand breaks and DNA-protein cross-links, resulting in the apoptotic cell death. Low-level insult with hydrogen peroxide has been shown to result in apoptotic cell death in HL-60 leukemia cells, while a high level insult has been shown to result in necrotic cell death in the same line of cells. (See generally, B. Halliwell and J. M. C. Gutteridge, Free Radicals in Biology and Medicine (Oxford: Clarendon Press, 1987); Cell Death, Ed. by M. Schwartz and B. A. Osborne (New York: Academic Press, 1995), especially Chapter IX (and subchapter "Induction of Apoptosis"); the disclosures of both of which are incorporated herein by reference). Apoptosis can also be induced by macromolecular synthesis inhibitor (protease or protein synthesis inhibitors), direct DNA damage (e.g., radiation, UV irradiation, thermal radiation), hydrogen peroxide, and cytotoxic drugs, and combinations thereof (generally described in Cell Death).

Recent research also has shown that a decrease in the intracellular pH, $pH_i$, of the cell (acidification of intracellular milieu) in the range of 1 pH unit can result in apoptosis. Such a change could be initiated by a change of the external pH, prompted, for example, by electrochemical reactions at the electrodes or by use of a pH-altering compound. For example, D. Perez-Sala et al., (J Biol Chem 1995, 270(11) :6235–42) shown that lovastatin induced apoptosis in HL-60 cells is associated with intracellular acidification with a decrease in $pH_i$ by 0.9 pH units. In another study H J Park et al, (Eur J Cancer 1996, 32A(3):540–6) reported effects of ionomycin ($Ca^{2+}$ ionophore, causing increase in intracellular $Ca^{2+}$) and intracellular pH in the range of 6.7–7.2 on apoptosis in HL-60 cells, with a peak increase at $pH_i$ 6.8–6.9. The control of $pH_i$ was achieved by changing the pH of the media and by interfering with the $pH_i$ regulatory mechanisms. Other recent studies discuss effects of an increase in intracellular $Ca^{2+}$ concentration with and without cell acidification, or a decrease in the internal superoxide ion $O_2^-$ concentration. All of these changes can be mediated and/or enhanced by electrical means; thus, a combination of chemical insult and use of electrochemical treatment, or in situ electrical generation of a cytotoxic compound, can be useful and fall within the scope of the present invention. Among other methods, flow cytometry can be used to evaluate the effects of treatment in vitro, as it can be used to measure internal pH and $Ca^{2+}$, as well as the percentage of surviving cells, percentage of apoptotic cells, and percentage of necrotic cells in the whole cell population. Apoptosis can also be investigated using light microscopy, gel electrophoresis and various biochemical assays. Still further, microanalytical techniques, such as described by D. R. Walt, "Bead-based Fiber-Optic Arrays," Science, vol. 287, Jan. 21, 2000, 451–2 (and references cited therein, the disclosures of which are incorporated herein by reference), can be used to measure DNA or certain chemical identifiers as an indication of the state of the cell (e.g., DNA from a necrotic cell can be sensed in the extracellular medium).

In another embodiment the potential can be controlled by sensing pH or $pO_2$ or another measurable parameter instead of, or in addition to, the electrode potential. The material engineering of the electrodes would be important for future research in this area: for example, platinum is a good electrode material for hydrogen evolution, while iridium oxide is a good electrode material for oxygen evolution, which means that those reactions happen at lower electrode potentials than for other electrode materials.

While there have been disclosed preferred embodiments of the inventions, it is to be understood that many changes may be made therein without departing from the spirit of the invention. Thus, while we have disclosed means to regulate the voltage applied to the electrodes, in lieu thereof, use may be made of means to regulate the current flowing through the tumor to optimize the yield of cytotoxic agents having the greatest efficacy.

What we claim is:

1. Apparatus for generating in situ in a tissue a cytotoxic agent which destroys the tissue, the apparatus comprising:
   A. at least two electrodes for placement within or near the tissue;
   B. a mechanism for applying a voltage across the electrodes to cause a current to flow through the tissue, so as to bring about an electrochemical reaction controllable by adjusting at least one of
      (i) the voltage, and
      (ii) the current, wherein the electrochemical reaction yields said cytotoxic agent.

2. Apparatus as set forth in claim 1 further including a reagent delivery mechanism for delivering to the tissue a reagent which, when current flows through the tissue, reacts with the material of at least one of the electrodes to produce said agent.

3. Apparatus as set forth in claim 2 in which said reagent is an electrolyte.

4. Apparatus as set forth in claim 3 in which said electrode is made of platinum and said electrolyte is ammonium chloride.

5. Apparatus as set forth in claim 2 in which at least one electrode is hollow to form a pipe for delivering said reagent to said tissue.

6. Apparatus as set forth in claim 1 further including a sensor to detect at least one quantity related to cytotoxicity to control at least one of the current and the voltage to optimize the efficacy of the agent.

7. Apparatus as set forth in claim 1 in which at least one of the electrodes is formed from a metal in the platinum class.

8. Apparatus as set forth in claim 2 in which at least one of the electrodes is formed from titanium, and said reagent is reactive therewith.

9. Apparatus as set forth in claim 1 further including a substance delivery mechanism for delivering to the tissue a photosensitive substance, and an optical illumination mechanism to illuminate the substance.

10. A kit for treating specified tissue in a patient, the kit comprising:
    A. at least one working electrode and at least one counterelectrode, each electrode adapted to be positioned within or near said tissue;
    B. a voltage generation mechanism for generating a voltage effective to induce a current between the electrodes, at least one of the current and the voltage being selected so as to cause generation of a cytotoxic compound from a precursor;
    C. a regulation mechanism for regulating at least one of the voltage across, and the current through, the electrodes;
    D. a precursor of a cytotoxic compound having cytotoxic activity against the tissue; and
    E. a precursor introduction mechanism for introducing the precursor into the patient into or near the tissue, the precursor being activated by at least one of
       (i) the current,
       (ii) the voltage,
       (iii) reaction with one of the electrodes, and
       (iv) illumination from a light source.

11. The kit of claim 10, wherein at least one of said electrodes is adapted to receive a fiber optic for delivering light into or near said tissue effective to activate said precursor.

12. The kit of claim 10, wherein one of said electrodes is hollow and porous and said precursor is introduced thereinto.

13. The kit of claim 10, wherein said voltage is regulated in a pulsed manner effective to deliver pulsed dosages of said precursor.

14. The kit of claim 10, wherein said voltage is regulated in a pulsed manner effective to activate said precursor in pulsed dosages.

15. A method for treating a tissue in a patient, the method comprising the steps of:
    A. establishing an in vivo current passing through or near the tissue; the current causing at least one of
       (i) generation of a cytotoxic agent from a precursor of a compound having cytotoxic activity against the tissue, and
       (ii) activation of a compound having cytotoxic activity against the tissue;
    B. providing at least one of the precursor and the compound in or near the tissue; and
    C. activating at least one of the precursor and the compound to be cytotoxic.

16. The method of claim 15, wherein said precursor is activated by said current.

17. The method of claim 15, wherein said current is provided by electrodes and said precursor is activated by reaction with at least one of said electrodes.

18. The method of claim 15, wherein said precursor is activated by light.

19. The method of claim 15, comprising a plurality of different precursor compounds.

20. The method of claim 15, wherein said activating is variable.

21. The method of claim 15, wherein an amount and/or potency of precursor activated is monitored in vivo.

22. The method of claim 21, wherein the activation of the precursor is regulated as a function of the monitored amount and/or potency of activated compound, or regulated as a function of another quantity related to the cytotoxic effect.

23. The method of claim 17, wherein said reaction is catalytic.

24. The method of claim 17, wherein said electrode is consumed by reaction with said precursor.

25. The method of claim 15, wherein said precursor comprises a metal.

26. The method of claim 25, wherein said metal is selected from the group consisting of Pt, Pd, Ru, Rh, Os, Ir, and mixtures thereof.

27. The method of claim 17, wherein said activated compound comprises a metal.

28. The method of claim 27, wherein said metal is selected from the group consisting of Pt, Pd, Ru, Rh, Os, Ir, and mixtures thereof.

29. The method of claim 15, wherein the patient is a human.

30. The method of claim 15, wherein the patient is a non-human.

31. The method of claim 19, wherein at least two compounds are administered simultaneously.

32. The method of claim 31, wherein said compounds are activated simultaneously.

33. The method of claim 31, wherein said compounds are activated serially.

34. The method of claim 19, wherein at least two compounds are administered serially.

35. Apparatus as set forth in claim 1, wherein the tissue is tumorous.

36. A method as set forth in claim 15, wherein the tissue is tumorous.

37. A method for generating in situ in a tissue a cytotoxic agent which destroys the tissue, the method comprising the steps of:

A. positioning at least two electrodes within or near the tissue; and

B. applying a voltage across the electrodes to cause a current to flow through the tissue, so as to bring about an electrochemical reaction controllable by adjusting at least one of
   (i) the voltage, and
   (ii) the current, wherein the electrochemical reaction yields said cytotoxic agent.

38. The method of claim 37 further including the step of delivering to the tissue a reagent which, when current flows through the tissue, reacts with the material of at least one of the electrodes to produce the cytotoxic agent.

39. The method of claim 38 wherein the reagent is an electrolyte.

40. The method of claim 39 wherein the electrode is made of platinum and the electrolyte is ammonium chloride.

41. The method of claim 38 wherein at least one electrode is hollow to form a pipe for delivering the reagent to the tissue.

42. The method of claim 37 further including the step of detecting at least one quantity related to cytotoxicity, so as to control at least one of the voltage and the current, to optimize the efficacy of the agent.

43. The method of claim 37 wherein at least one of the electrodes is formed from a metal in the platinum class.

44. The method of claim 38 wherein at least one of the electrodes is formed from titanium, and the reagent is reactive therewith.

45. The method of claim 37 further including the steps of
   (i) delivering to the tissue a photosensitive substance, and
   (ii) illuminating the substance.

* * * * *

UNITED STATES PATENT AND TRADEMARK OFFICE
CERTIFICATE OF CORRECTION

PATENT NO.    : 6,708,066 B2
DATED         : March 16, 2004
INVENTOR(S)   : Herbst et al.

It is certified that error appears in the above-identified patent and that said Letters Patent is hereby corrected as shown below:

Title page,
Item [76], Inventors, address should read as follows:
-- Ewa Herbst, P.O. Box 89, Edgewater, NJ 07020-0089; Benedict Aurian-Blajeni, 1068 South Main Street, Bellingham, MA 02019-1632 --.

Signed and Sealed this

Thirteenth Day of July, 2004

JON W. DUDAS
*Acting Director of the United States Patent and Trademark Office*